(12) United States Patent
Mansi et al.

(10) Patent No.: US 9,129,053 B2
(45) Date of Patent: Sep. 8, 2015

(54) METHOD AND SYSTEM FOR ADVANCED MEASUREMENTS COMPUTATION AND THERAPY PLANNING FROM MEDICAL DATA AND IMAGES USING A MULTI-PHYSICS FLUID-SOLID HEART MODEL

(71) Applicants: Tommaso Mansi, Westfield, NJ (US); Viorel Mihalef, Keasbey, NJ (US); Xudong Zheng, Plainsboro, NJ (US); Bogdan Georgescu, Plainsboro, NJ (US); Saikiran Rapaka, Eagleville, PA (US); Puneet Sharma, Rahway, NJ (US); Ali Kamen, Skillman, NJ (US); Dorin Comaniciu, Princeton Junction, NJ (US)

(72) Inventors: Tommaso Mansi, Westfield, NJ (US); Viorel Mihalef, Keasbey, NJ (US); Xudong Zheng, Plainsboro, NJ (US); Bogdan Georgescu, Plainsboro, NJ (US); Saikiran Rapaka, Eagleville, PA (US); Puneet Sharma, Rahway, NJ (US); Ali Kamen, Skillman, NJ (US); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 422 days.

(21) Appl. No.: 13/757,517

(22) Filed: Feb. 1, 2013

(65) Prior Publication Data
US 2013/0197884 A1    Aug. 1, 2013

Related U.S. Application Data

(60) Provisional application No. 61/593,500, filed on Feb. 1, 2012.

(51) Int. Cl.
*G06F 19/00* (2011.01)
*G06T 19/00* (2011.01)

(52) U.S. Cl.
CPC ............ *G06F 19/3437* (2013.01); *G06T 19/00* (2013.01); *G06T 2210/41* (2013.01)

(58) Field of Classification Search
CPC .......... G06T 19/20; G06T 19/00; G06G 7/60; G06G 7/57; G06F 19/00; G06F 17/50; G06F 19/3437; A61N 1/365
USPC .............. 703/6, 9, 11, 2; 345/420; 607/25, 17
See application file for complete search history.

(56) References Cited

U.S. PATENT DOCUMENTS 8,098,918 B2    1/2012   Zheng et al.
8,386,188 B2    2/2013   Taylor et al.
(Continued)

OTHER PUBLICATIONS

Dikici et al., "Quantification of Delayed Enhancement MR Images", In Proc. MICCAI 2004, LNCS 3216, pp. 250-257, 2004.
(Continued)

*Primary Examiner* — Kandasamy Thangavelu

(57) ABSTRACT

Method and system for computation of advanced heart measurements from medical images and data; and therapy planning using a patient-specific multi-physics fluid-solid heart model is disclosed. A patient-specific anatomical model of the left and right ventricles is generated from medical image patient data. A patient-specific computational heart model is generated based on the patient-specific anatomical model of the left and right ventricles and patient-specific clinical data. The computational model includes biomechanics, electrophysiology and hemodynamics. To generate the patient-specific computational heart model, initial patient-specific parameters of an electrophysiology model, initial patient-specific parameters of a biomechanics model, and initial patient-specific computational fluid dynamics (CFD) boundary conditions are marginally estimated. A coupled fluid-structure interaction (FSI) simulation is performed using the initial patient-specific parameters, and the initial patient-specific parameters are refined based on the coupled FSI simulation. The estimated model parameters then constitute new advanced measurements that can be used for decision making.

33 Claims, 12 Drawing Sheets

(56) References Cited

U.S. PATENT DOCUMENTS

| | | | |
|---|---|---|---|
| 2012/0022843 A1* | 1/2012 | Ionasec et al. | 703/9 |
| 2012/0041301 A1 | 2/2012 | Redel | |
| 2012/0072190 A1 | 3/2012 | Sharma et al. | |
| 2012/0121151 A1 | 5/2012 | Bernhardt et al. | |
| 2012/0203530 A1 | 8/2012 | Sharma et al. | |
| 2012/0310297 A1* | 12/2012 | Sweeney | 607/25 |
| 2013/0197881 A1* | 8/2013 | Mansi et al. | 703/2 |
| 2013/0226542 A1* | 8/2013 | Rapaka et al. | 703/2 |
| 2014/0022250 A1* | 1/2014 | Mansi et al. | 345/420 |

OTHER PUBLICATIONS

Peyrat et al., "A Computational Framework for the Statistical Analysis of Cardiac Diffusion Tensors: Application to a Small Database of Canine Hearts", IEEE TMI, 26(11): 1500-1514, 2007.

Mitchell et al., "A Two-Current Model for the Dynamics of Cardiac Membrane", Bulletin of Mathematical Biology, 65(5):767-793, 2003.

Powell, "Developments of NEWUOA for Minimization Without Derivatives", J. Num. Analysis, 2008.

* cited by examiner

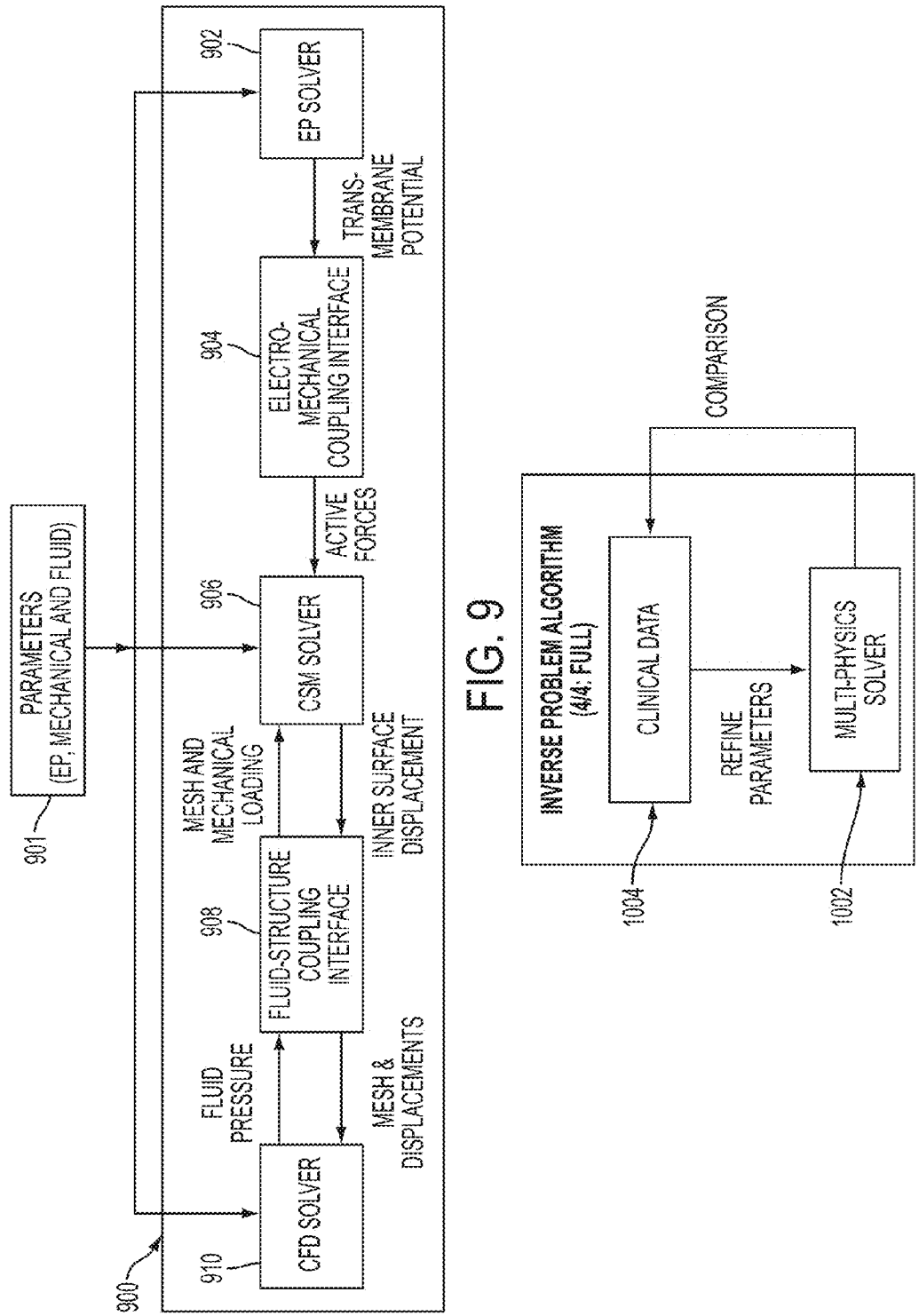

METHOD AND SYSTEM FOR ADVANCED MEASUREMENTS COMPUTATION AND THERAPY PLANNING FROM MEDICAL DATA AND IMAGES USING A MULTI-PHYSICS FLUID-SOLID HEART MODEL

This application claims the benefit of U.S. Provisional Application No. 61/593,500, filed Feb. 1, 2012, the disclosure of which is herein incorporated by reference.

BACKGROUND OF THE INVENTION

The present invention relates to the computation of advanced cardiac parameters from medical data and images by using a patient-specific multi-physics fluid-solid models of the heart.

The heart is the pump of life. The periodic contraction and relaxation cycle of the heart ensures blood circulation throughout the body. Heart diseases can affect the ventricle shape, the integrity of the muscle, the electrophysiology of the heart, etc., but the end result is incorrect or inadequate blood circulation in a patient. Hence, the ultimate goal of any cardiac therapy is to correct the blood flow, by acting on the various aspects of the cardiac system that may be affected, directly or indirectly, by existing pathologies in the patient.

Cardiac disease diagnosis and therapy planning are made difficult by the large variability in heart diseases. Every patient is unique. The variability observed among patients with the same disease is such that population-wise guidelines can be sub-optimal in terms of diagnosis, therapy outcome and complications for a specific patient. For example, patients with acute myocardium infarction can present with variable scar morphology and extent, which can influence the outcome of various cardiac therapies. Accordingly, a framework to assess the current state of the heart and the optimal therapy for a specific patient is desirable. Such a framework should be integrative and comprehensive, considering all major aspects of heart function, and focus on the end-result of any cardiac therapy, which is the restoration of normal blood flow.

BRIEF SUMMARY OF THE INVENTION

The present invention provides a method and system for computing advanced cardiac measurements from clinical images and data using a patient-specific multi-physics model. Embodiments of the present invention provide a simulation framework that can be utilized to estimate advanced cardiac measurements not accessible through standard clinical devices and optimize various cardiac therapies, such as open-heart therapies or electrophysiology therapies, in terms of cardiac blood flow. Embodiments of the present invention utilize a fluid-structure interaction framework that couples a multi-scale model of cardiac electrophysiology, a multi-scale model of cardiac biomechanics, and a computational fluid dynamics based model of cardiac blood flow together in order to estimate intrinsic cardiac parameters, such as tissue stiffness, active stress, electrical diffusion, etc., and predict heart blood flow after a cardiac therapy. Medical imaging data and non-imaging clinical data of a patient are used to adjust free parameters of the simulation framework, such that the patient-specific heart function is accurately reproduced in the computer simulation. These parameters are then used as advanced cardiac measurements by the user. Therapies can then be simulated by altering the patient-specific model in terms of heart shape to simulate surgical therapies, or dynamics to simulate electrophysiology therapies.

In one embodiment of the present invention, a patient-specific anatomical model of left and right ventricles is generated from medical image data of a patient. A patient-specific computational heart model is generated based on the patient-specific anatomical model of the left and right ventricles and patient-specific clinical data. The computational model comprises an electrophysiology component, a biomechanics component and a hemodynamics component. The patient-specific computational heart model is generated by determining initial patient-specific parameters of an electrophysiology model, determining initial patient-specific parameters of a biomechanics model, determining initial patient-specific computational fluid dynamics (CFD) boundary conditions, performing a coupled fluid-structure interaction (FSI) simulation using the initial patient-specific parameters of the electrophysiology model, the initial patient-specific parameters of the biomechanics model, and the initial patient-specific CFD boundary conditions, and refining the initial patient-specific parameters of the electrophysiology model, the initial patient-specific parameters of the biomechanics model, and the initial patient-specific CFD boundary conditions based on the coupled FSI simulation. The refined parameters define a set of advanced cardiac measurements. At least one cardiac therapy is simulated using the patient-specific computational heart model.

These and other advantages of the invention will be apparent to those of ordinary skill in the art by reference to the following detailed description and the accompanying drawings.

BRIEF DESCRIPTION OF THE DRAWINGS

FIG. 9 illustrates a framework for implementing the coupled Fluid-Structure Interaction (FSI) simulation according to an embodiment of the present invention;

FIG. 10 illustrates a framework for refining the patient-specific parameters of the computation heart model according to an embodiment of the present invention;

DETAILED DESCRIPTION

The present invention relates to a method and system to compute advanced cardiac measurements and plan cardiac therapies using a patient-specific multi-physics fluid-solid heart model that is personalized for a patient based on preoperative medical image data, such as magnetic resonance imaging (MRI) and/or Ultrasound data, and non-imaging clinical data, such as echo cardiogram (ECG) and pressure measurements. Embodiments of the present invention are described herein to give a visual understanding of the cardiac therapy simulation methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a simulation framework that can be utilized to estimate advanced measurements, which correspond to the patient-specific values of the simulation framework, and to optimize various cardiac therapies, such as open-heart therapies or electrophysiology therapies, in terms of cardiac blood flow. Embodiments of the present invention utilize a fluid-structure interaction framework that couples a multi-scale model of cardiac electrophysiology, a multi-scale model of cardiac biomechanics, and a computational fluid dynamics based model of cardiac blood flow together in order to predict heart blood flow after a cardiac therapy. Medical imaging data and non-imaging clinical data of a patient are used to adjust free parameters of the simulation framework, such that the patient-specific heart function is accurately reproduced in the computer simulation. The estimated parameters constitute an output of the system, and are referred to herein as "advanced cardiac measurements". Therapies can then be simulated by altering the patient-specific model in terms of heart shape to simulate surgical therapies, or dynamics to simulate electrophysiology therapies.

Figure 1:
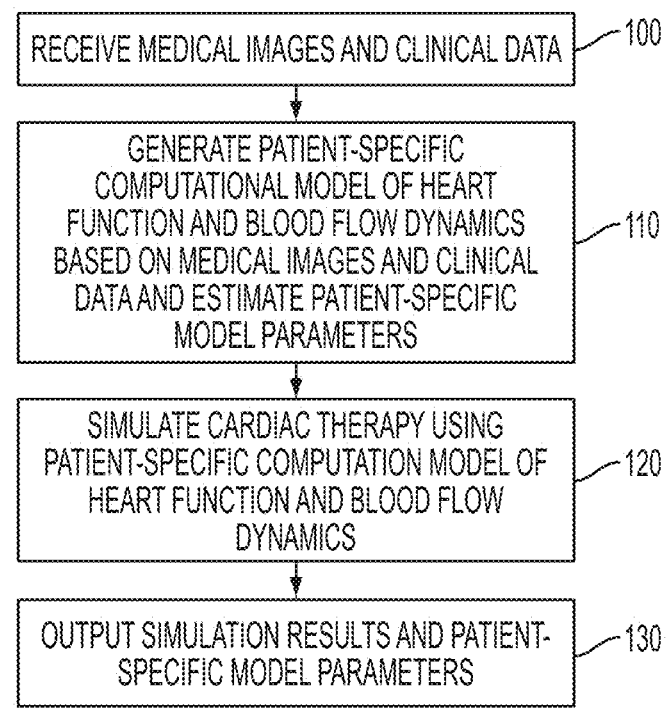
FIG. 1 illustrates a method for patient-specific estimation of advanced cardiac measurements and planning and simulation of cardiac therapies according to an embodiment of the present invention.

FIG. 1 illustrates a method for patient-specific advanced cardiac parameters estimation and therapy planning according to an embodiment of the present invention. As illustrated in FIG. 1, at step 100 medical images and clinical data of a patient are received. The medical images can be 3D preoperative images of the patient. The medical images may be a dynamic sequence of medical images acquired over at least one complete heart cycle. In advantageous embodiments of the present invention, the medical images can be MRI images and/or ultrasound images, but the present invention is not necessarily limited to these imaging modalities. The medical images may be received directly from a medical imaging device, such as an MR or ultrasound scanner, or the medical images may be received by loading stored medical images of a patient. The clinical data can include non-imaging patient-specific measurements, such as ECG, pressure measurements, etc. Pressure measurements may be acquired by catheter-based invasive pressure measurements or cuff pressure measurements. At step 110, a patient-specific computational model of heart function and blood flow dynamics is generated based on the medical images and the clinical data for the patient. At step 120, a cardiac therapy is simulated using the patient-specific computational model of heart function and blood flow dynamics. At step 130, the advanced measurements estimated at step 110 are output and the simulation results representing the heart function and blood flow of the patient after the simulated therapy calculated at step 120 are output. These simulation results can be used for better diagnosis and also to plan, select, or optimize various cardiac therapies, including open heart therapies and/or electrophysiology therapies.

Figure 2:
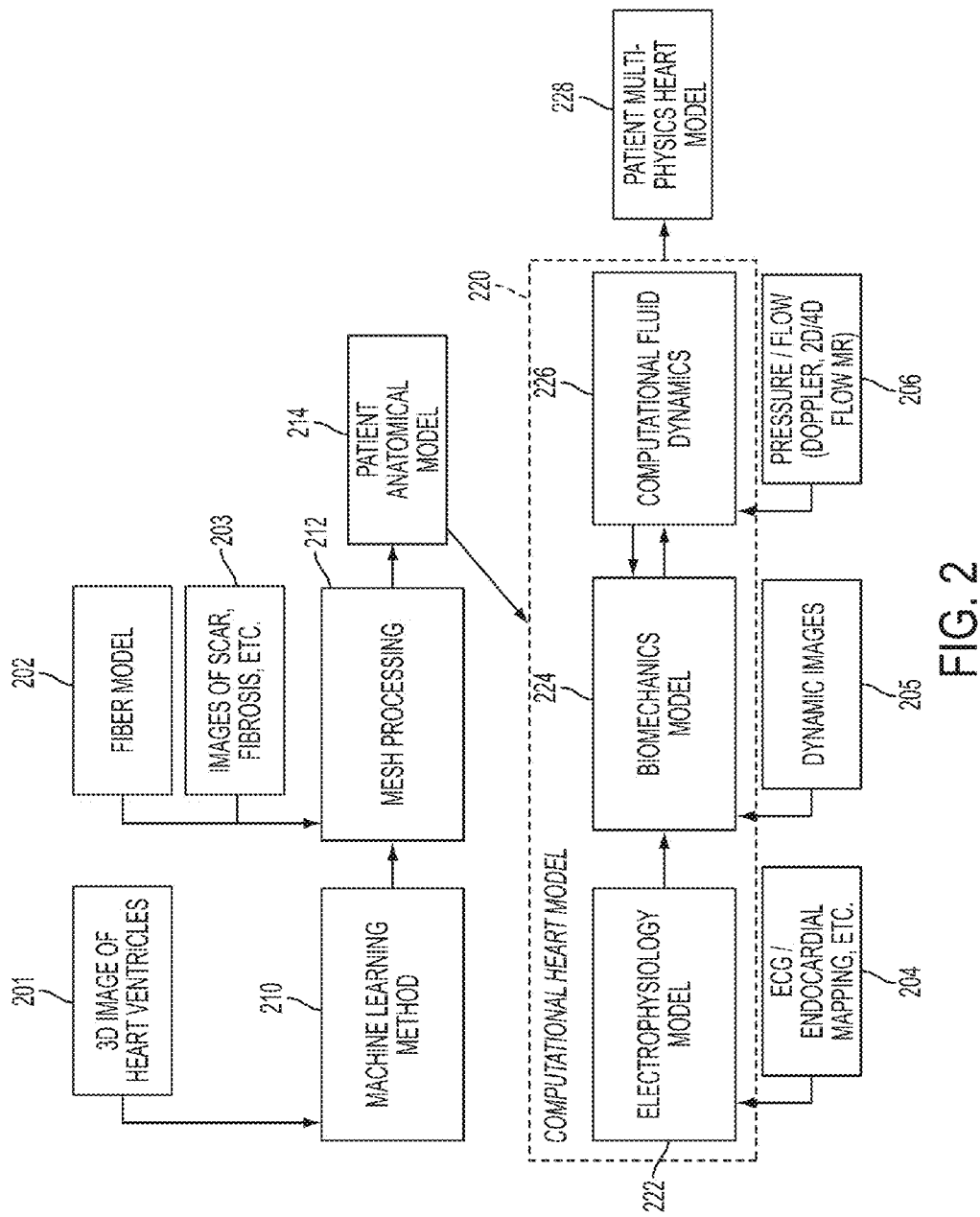
FIG. 2 illustrates a framework for generating a patient-specific computational heart model according to an embodiment of the present invention.

FIG. 2 illustrates a framework for generating a patient-specific computational heart model according to an embodiment of the present invention. The framework illustrated in FIG. 2 can be used to implement the first stage (step 110) of the method of FIG. 1. As illustrated in FIG. 2, the construction of the patient-specific model relies on preoperative data including a 3D medical image of the heart ventricles 201, a fiber model 202, medical images of scars, fibrosis, etc. in the ventricles 203, patient-specific clinical data including ECG, endocardial mappings, etc., dynamic medical images 205, and pressure/flow data (e.g., Doppler or 2D/4D flow MR images) to set free parameters to generate two models: a comprehensive model of the patient's heart anatomy 214 and a generative, computational model of heart function and blood flow 228, which is then used to compute clinical parameters such as ejection fraction, Q-R-S wave complex (QRS), blood flow patterns, etc. At step 210, a machine learning method is used to detect patient-specific anatomical models of the left ventricle (LV) and the right ventricle (RV) from a 3D medical image 201. At step 212, mesh processing is used to fuse the detected LV and RV models into a single volumetric mesh, map spatial information, such as scars, grey zones, and fibrosis, from the input images 203 to the mesh, and map the patient-specific fiber model 204 to the mesh, resulting in the patient-specific anatomical model 214. At step 220, patient-specific parameters are estimated for the computational heart model, resulting in the patient-specific multi-physics heart model 228. The computational heart model includes an electrophysiology model, biomechanics model, and computational fluid dynamics (CFD) component. Step 220 includes sub-steps 222, 224, and 228. At step 222, patient-specific parameters of the electrophysiology model are determined based on the ECG and/or endocardial mapping data 204. At step 224, patient-specific parameters of the biomechanics model are determined based on the dynamic medical images 205. At step 226, patient-specific parameters are determined for CFD boundary conditions based on pressure and/or flow data 206. The steps of the framework of FIG. 2 are described in greater detail below. In an advantageous embodiment described herein, only the left and right ventricles are modeled. Atria, arteries, and body circulation are modeled as boundary conditions of the computational heart model.

Figure 3:
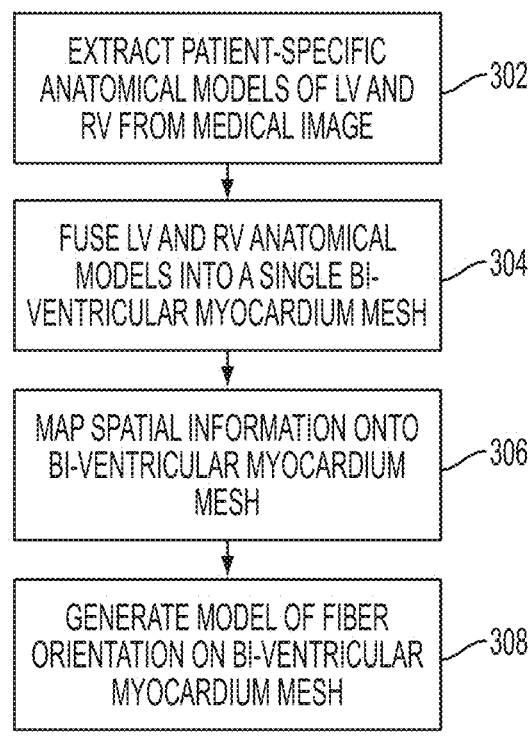
FIG. 3 illustrates a method for generating the patient-specific anatomical model of the left and right ventricles according to an embodiment of the present invention.

FIG. 3 illustrates a method for generating the patient-specific anatomical model of the left and right ventricles according to an embodiment of the present invention. The method of FIG. 3 provides additional details for implementing steps 210 and 212 of FIG. 2 in order to generate the patient-specific anatomical model 214. At step 302, anatomical models of the LV and RV are extracted from the medical images. In an advantageous embodiment, the LV and RV anatomical models show patient-specific heart morphology and dynamics, and are calculated automatically from MRI or ultrasound images (US). The LV and RV models can be detected in any preoperative images (e.g., US or cardiac MR) that cover the entirety of both cardiac ventricles. The LV and RV models can be extracted by segmenting the left endocardium, right endocardium, epicardium, and left and right outflow tract using a marginal space-learning based machine learning method. Obtained triangulations (meshes) are automatically labeled according to the anatomy they represent for subsequent processing.

For each of the LV and the RV, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve a robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

At step 304, the patient-specific LV and RV models are fused into a single bi-ventricular myocardium volumetric mesh. In a possible implementation, the LV and RV anatomies extracted can be fused together. The resulting closed surface is used to create a volumetric, tetrahedral mesh on which vertices are tagged into surface zones according to the underlying anatomy.

At step 306, spatial information is mapped onto the bi-ventricular myocardium mesh. Spatial information, such as scars, grey zones, and fibrosis can be identified in images, such as late delayed-enhancement MR images and mapped onto the bi-ventricular myocardium mesh. For example, scar locations and extent can be segmented in delayed-enhancement MR images using the method described in Dikici et al, "Quantification of Delayed Enhancement MR Images", In Proc. MICCAI 2004, LNCS 3216, pp 250-257, 2004, which is incorporated herein by reference. The scar information is mapped onto the bi-ventricular myocardium mesh by tagging the tetrahedral elements that lie within the segmented scar regions. This spatial information is important to simulate the electrical wave around scars, in particular for wave-reentry assessment, but also the impaired contractility due to dead tissue.

At step 308, model of fiber orientation is generated on the bi-ventricular myocardium mesh. In one embodiment, in-vivo diffusion tensor (DT) MR images of the patient's cardiac fibers are directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", IEEE TMI, 26(11):1500-1514, 2007, which is incorporated herein by reference, is used to reorient the tensors once the tensors are registered to the anatomical model.

In another embodiment, if no in-vivo DT MRI are available, the model of fiber orientation may be computed directly from the anatomical model using a rule-based method. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle $\alpha$, i.e. their angle with respect to the short axis plane, varies linearly across the myocardium, from $-70$ on the epicardium to $+70$ on the endocardium. Similarly, the sheet direction, which is defined by the angle $\beta$ with respect to the outward transmural axis, varies transmurally from $+45$ on the epicardium to $-45$ on the endocardium. $\alpha$ and $\beta$ are computed for each point of the volumetric bi-ventricular myocardium mesh between the apex and basal plane based on the geodesic distance to the endocardia and epicardia identified by the facet tags: $\alpha = (d_{epi}\alpha_{endo} + d_{endo}\alpha_{epi})/(d_{endo} + d_{epi})$, where $d_{epi}$, $d^{endo}$, $\alpha_{epi}$, and $\alpha_{endo}$ are the distances and angles at the endocardium and epicardium, respectively. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. For orthonormality preservation, the interpolation can be performed using a Log-Euclidean framework.

Figure 4:
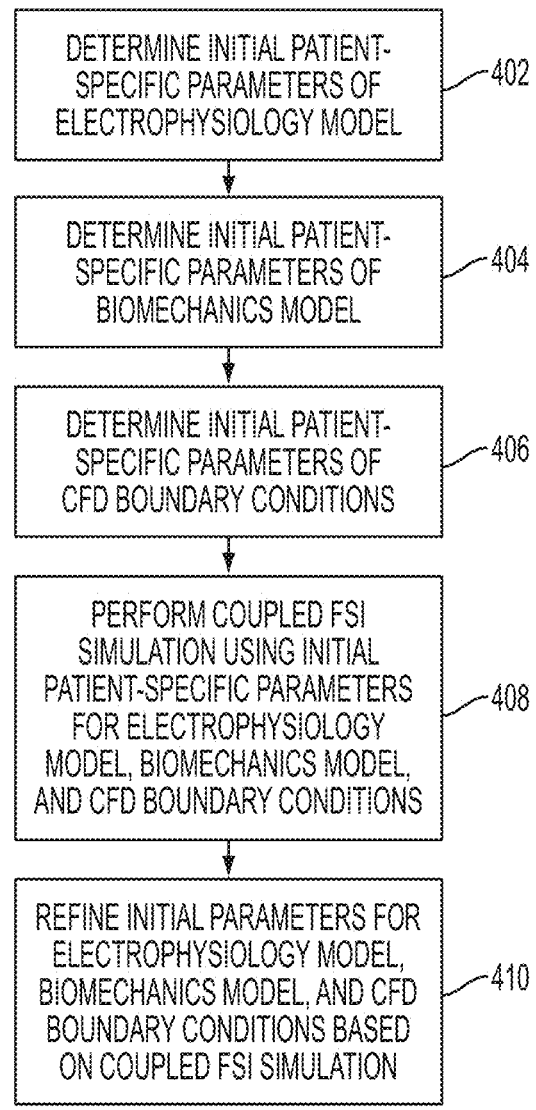
FIG. 4 illustrates a method of determining patient-specific parameters of the computational heart model according to an embodiment of the present invention.

Once the patient-specific anatomical model is generated, then patient-specific anatomical model is provided as an input to the computational heart model solver module (step 220 of FIG. 2). The computational heart solver module includes three components (electrophysiology solver, biomechanics solver, and CFD solver) that are solved sequentially at every time step to simulate the fluid-structure interactions happening during a heartbeat. In order to achieve a patient-specific computational heart model, patient-specific parameters are determined for each of the components of the computational heart model solver. FIG. 4 illustrates a method of determining patient-specific parameters of the computational heart model according to an embodiment of the present invention. The method of FIG. 4 uses a marginal approach to personalize the parameters of the electrophysiology model, the biomechanics model, and the boundary conditions for CFD. The method of FIG. 4 can be used to implement step 220 of FIG. 2, including substeps 222, 224, and 226, in order to generate the patient-specific multi-physics heart model 228, which can then be used to simulate various cardiac therapies.

Referring to FIG. 4, at step 402, initial patient-specific parameters of the electrophysiology model are generated. In an advantageous embodiment the cardiac electrophysiology (EP) is computed by solving a Mitchell and Schaeffer model of cardiac action potential on the patient's heart anatomy with finite element models. The Mitchell and Schaeffer model is described in Mitchell et al., "A Two-Current Model for the Dynamics of Cardiac Membrane", *Bulletin of Mathematical Biology*, 65(5):767-793, 2003, which is incorporated herein by reference. A diffusion term is added into the original Mitchell and Schaeffer model to mimic wave propagation throughout the patient-specific anatomical model. The following reaction-diffusion equation is solved to compute the generation and propagation of the action potential over patient's bi-ventricular geometry:

$$\frac{\partial v}{\partial t} = \nabla \cdot K \nabla_v + \frac{hv^2(1-v)}{\tau_{in}} - \frac{v}{\tau_{out}} + J_{stim}(t) \quad (1)$$

$$\frac{\partial h}{\partial t} = \begin{cases} (1-h)/\tau_{open} & \text{if } v < v_{gate} \\ -h/\tau_{close} & \text{if } v \geq v_{gate}, \end{cases}$$

where v(t) is the trans-membrane potential, h(t) is a gating function, K is the anisotropic diffusivity matrix, $J_{stim}(t)$ is an external stimulus (a CRT lead for instance), and $T_{in}$, $T_{out}$, $T_{close}$, $T_{open}$ are free parameters that are directly related to the shape of the action potential. The model is paced at the septum with a user-defined frequency, which can be estimated from ECG signals.

In an advantageous implementation, the electrophysiology (EP) model can be extended to consider Purkinje fibers. In general, the anatomical structures of the Purkinje network cannot be extracted from medical imaging modalities. In order to mimic the fast propagation of electrical waves along the Purkinje fibers while keeping the problem tractable, embodiments of the present invention implement a "macro-scale" electrophysiology model of Purkinje fibers. For this model, it is assumed that the Purkinje fibers are evenly distributed on the entire endocardial surface. Thus, the Purkinje fibers can be modeled as a "continuous" membrane rather than a complex network. The above-described Mitchell-Schaeffer equations can be solved on this membrane using two-dimensional finite element formulation. In order to take into account the complex three dimensional shape of the endocardial surface, the finite element formulation is first built on each local, planar coordinate and then is rotated back into the global coordinate system to perform the final assembly. The fast propagation is implemented by setting a high diffusion coefficient $K_{Purkin}$. The coupling between the "macro-scale" Purkinje fiber model and the myocardium is implemented through boundary conditions. Here, one way coupling is employed to link the Purkinje fiber with the myocardium. At each time step, the electrophysiological equation (Equation 1) is first solved on the endocardial triangulation defining the domain of the macro-scale Purkinje fiber. Since the endocardial triangulation has one-to-one mapping with the tetrahedral vertices at the endocardium, Dirichlet boundary conditions can be specified for the myocardium so that the potential at these tetrahedral nodes are set equal to the corresponding triangulation nodes. The equations are then solved on the entire myocardium. Additional details regarding the electrophysiology model are described in U.S. patent application Ser. No. 13/754,174, entitled "Method and System for Patient Specific Planning of Cardiac Therapies on Preoperative Clinical Data and Medical Images", filed Jan. 30, 2013, which is incorporated herein by reference.

In order to personalize the electrophysiology model to a specific patient, the parameters of the electrophysiology model are adjusted using inverse problem methods based on the observed clinical data and medical image data for the patient. ECG and endocardial mapping are used to adjust tissue diffusivity K and action potential duration, mainly controlled by the parameter $\tau_{close}$, at every node of the anatomical model. For example, the simulated QRS (heartbeat) can be aligned with measured QRS by adjusting tissue diffusivity K. If endocardial mappings are available, inverse problem methods can be used to estimate tissue conductivity and $\tau_{close}$ by comparing the simulated isochrones and potentials with measurements. Additionally, dynamic images can be used to adjust electrophysiology overall synchrony by minimizing the difference of the cardiac motion computed from the electrophysiology model and the observations, and bundle branch blocks can be simulated by modifying the activation times of the left and right ventricles.

Figure 5:
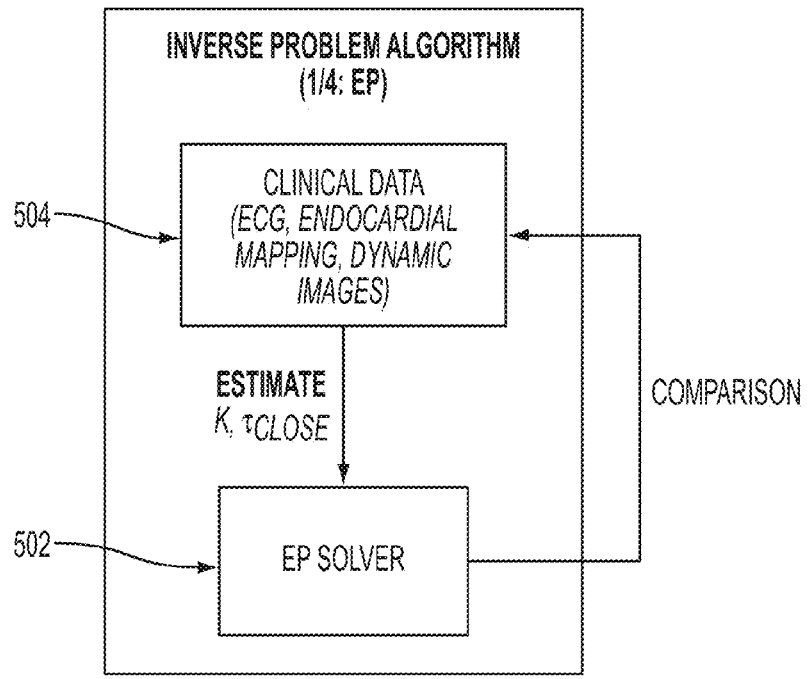
FIG. 5 illustrates a framework for determining the initial electrophysiology model parameters according to an embodiment of the present invention.

For computational efficiency, a marginal approach is employed to estimate the initial EP parameters. FIG. 5 illustrates a framework for determining the initial electrophysiology model parameters according to an embodiment of the present invention. As shown in FIG. 5, a first estimate of the electrophysiology model parameters is obtained by computing cardiac EP only using the EP solver 502, i.e. uncoupling the EP solver 502 from the entire system. In particular, the EP solver 502 simulates only cardiac electrophysiology using Equation (1), the output simulated cardiac electrophysiology from the EP solver 502 is compared to the clinical data 504, and the parameters (K, $\tau_{close}$) of the electrophysiology model are adjusted using an inverse problem algorithm to best match the simulated cardiac electrophysiology with the clinical data 504, resulting in the initial patient-specific parameters for the electrophysiology model. The estimated initial parameters for the electrophysiology model will then be refined in step 410, as described below.

Returning to FIG. 4, at step 404, initial patient-specific parameters of the biomechanics model are determined. Cardiac biomechanics is computed by solving the dynamics equation using finite-element methods:

$$M\ddot{U} + C\dot{U} + KU = F_c + F_p + F_b. \quad (2)$$

In Equation 2, U(t) is the position of the node of the anatomical model, M is a diagonal mass matrix (mass density ρ=1.070 g/mL), and C is a Rayleigh damping matrix. K is the stiffness matrix of myocardium tissue. In a possible embodiment, the stiffness matrix K can be modeled using co-rotational transverse isotropic elasticity to increase computational efficiency while coping with large deformations and tissue anisotropy. The model is controlled by the Young Modulus E and the Poisson ratio v, which is set to 0.488 to model tissue incompressibility. In other possible embodiments, various types of non-linear hyperelastic models, such as a Mooney-Rivlin model or a Holzapfel-Ogden model, can be used to model the passive tissue properties of the myocardium tissue. Additional details regarding modeling the passive tissue properties are described in U.S. patent application Ser. No. 13/754,174, entitled "Method and System for Patient Specific Planning of Cardiac Therapies on Preoperative Clinical Data and Medical Images", filed Jan. 30, 2013, which is incorporated herein by reference.

Depolarized cardiac cells contract according to an active force $F_c(t)$ controlled by the trans-membrane potential v(t). That force increases exponentially as the cell depolarizes, at a rate $+k_{ATP}$ related to the rate of ATP binding, to reach a maximum contraction strength $\sigma_0$ that is controlled by the user. When the cell repolarizes, the force fades away exponentially at a rate $-k_{RS}$ related to the rate of ATP release. Additional details regarding modeling the active force $F_c(t)$ of cell contraction are described in U.S. patent application Ser. No. 13/754,174, entitled "Method and System for Patient Specific Planning of Cardiac Therapies on Preoperative Clinical Data and Medical Images", filed Jan. 30, 2013, which is incorporated herein by reference.

The base of the anatomical model is attached using stiff springs $F_b(t)$ to mimic the compliance of the atria and arteries. A pericardium constraint can also be applied to keep the heart fixed in space. Nodes of the anatomical models that go outside the allowed region of the pericardium bag are moved back by applying a spring force, also gathered in the global vector $F_b(t)$. Additional details regarding the base stiffness parameter and the pericardium constraint are described in U.S. patent application Ser. No. 13/754,174, entitled "Method and System for Patient Specific Planning of Cardiac Therapies on Preoperative Clinical Data and Medical Images", filed Jan. 30, 2013, which is incorporated herein by reference. $F_p(t)$ is a pressure applied on the endocardial surface of each ventricle resulting from the blood flow through the ventricles. That pressure is directly computed using the CFD solver described below.

Figure 6:
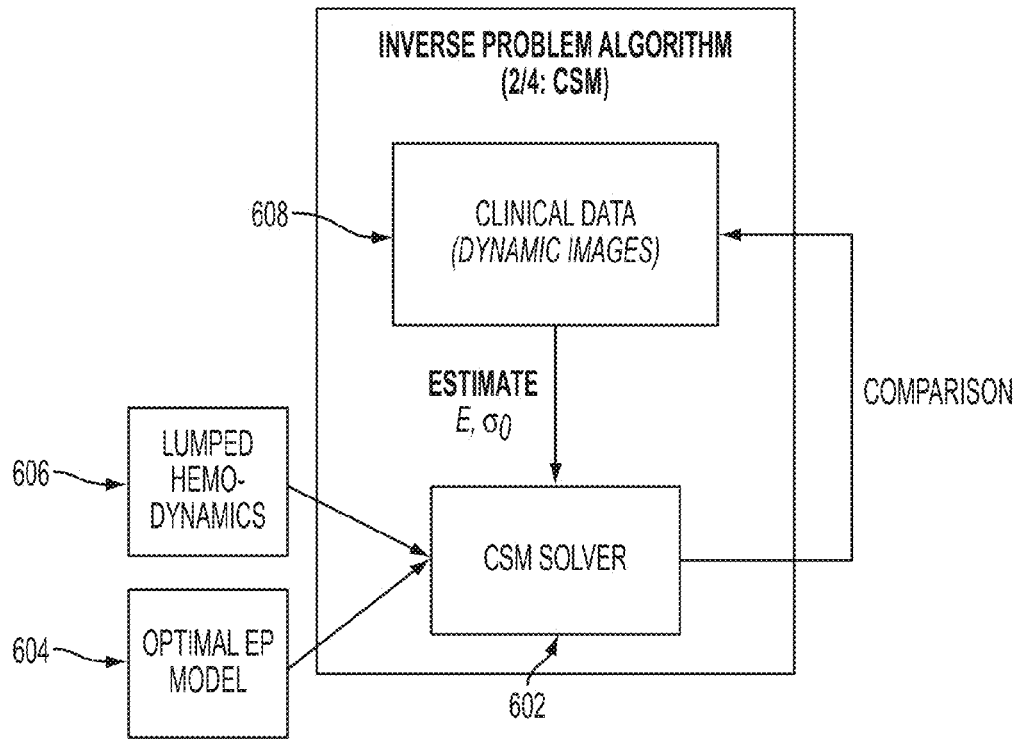
FIG. 6 illustrates a framework for determining the initial patient-specific parameters of the biomechanical model.

In order to personalize the biomechanical model, the parameters of the biomechanical model ($E$, $\sigma_0$) are adjusted from the dynamics images by comparing the observed cardiac dynamics with the simulated motion of the ventricles. For example, the active contraction strength $\sigma_0$ can be adjusted from the motion observed during systole, and the tissue stiffness $E$ can be adjusted to match the dynamics observed during passive systole. FIG. 6 illustrates a framework for determining the initial patient-specific parameters of the biomechanical model. As shown in FIG. 6, the initial patient-specific parameters of the EP model 604 (determined at step 402) are used to compute the trans-membrane potential that controls the active force $F_c$. In order to preliminary estimate the patient-specific biomechanical parameters without requiring the CFD solver, lumped models of heart hemodynamics 606 are used to model Atrial and aortic pressures ($F_p$). In particular, the aortic pressure is computed using a 3-element Windkessel model, whose parameters can be estimated automatically from pressure catheterization and volume measurements. Additional details regarding the lumped models of heart hemodynamics are describes in U.S. patent application Ser. No. 13/754,174, entitled "Method and System for Patient Specific Planning of Cardiac Therapies on Preoperative Clinical Data and Medical Images", filed Jan. 30, 2013, which is incorporated herein by reference. The biomechanics or computational solid mechanics (CSM) solver 602 simulates the motion at each node of the anatomical model based on the input from the EP model 604 and the lumped hemodynamics model 606. The simulated motion is compared with the observed clinical data 604 (e.g. dynamic images) and the parameters ($E$, $\sigma_0$) of the biomechanics model are adjusted using an inverse problem algorithm to best match the simulation results to the observed clinical data 604, resulting in the initial patient-specific biomechanics model parameters. The initial parameters are then used as starting point of the fully coupled model, as described below.

Returning to FIG. 4, at step 406, initial patient-specific CFD boundary conditions are determined. The CFD models blood as a Newtonian fluid, with the flow dynamics governed by the Navier-Stokes equations. These equations can be solved numerically with a fractional step method on a rectangular grid, inside which the cardiac walls are embedded using a level set. The level set helps imposing the correct boundary conditions using the ghost fluid method, and is also used to compute the face fractions employed by the implicit solvers (e.g., the approximate projection method for the pressure). As opposed to one-way (wall to fluid) CFD calculations, embodiments of the present invention perform two-way (wall-fluid-wall) interactions. For such two-way interactions, a standard FSI framework is used: the wall kinematics imposes Dirichlet boundary conditions on the fluid velocity and the fluid pressure imposes forces back to the wall.

According to an advantageous embodiment of the present invention, the following boundary conditions are used, in order to achieve personalized CFD computations:

WALLS—The ghost fluid method is used to impose Dirichlet boundary conditions for the velocity and a finite volume cell flux balance using Neumann boundary conditions for the pressure;

INLETS—The mitral and tricuspid valves are used to impose specialized boundary conditions during all cardiac phases, as follows: during systole and isovolumetric phases, they are closed and the boundary conditions are set to no-slip wall; during diastole they are open, but their closed geometric position is used to impose Dirichlet boundary conditions for the personalized atrial pressures;

OUTLETS—The aortic and pulmonary valves are used to impose specialized boundary conditions during all cardiac phases, as follows: during diastole and isovolumetric phases, they are closed and the boundary conditions are set to no-slip wall; during systole they are open, but their closed geometric position is used to impose Dirichlet boundary conditions for the personalized aortic pressures. Such pressures can be obtained either from patient-specific clinical measurements, or from generative boundary conditions, based on a lumped model of arterial pressure like Windkessel models. Parameters of the Windkessel model can be personalized from pressure catheterization and arterial flow.

Figure 7:
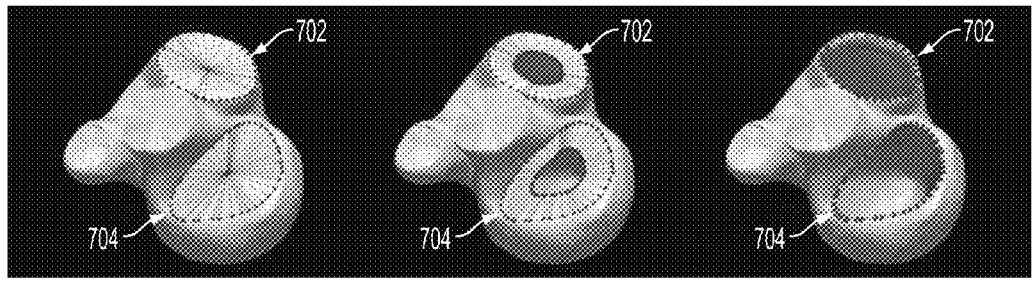
FIG. 7 illustrates a synthetic model of valve dynamics for CFD boundary conditions.

Valve kinematics can be modeled using a geometric approach as they are often difficult to visualize from patient-specific data. Each valve is defined as a triangulated patch prescribed by an annulus curve automatically detected on the outflow and inflow tracts of the ventricles. Machine learning approaches can be used to estimate the annuli from the images. Owing to point correspondence, the annuli can be tracked over-time, to determine the dynamics of the valve. Valve closure and opening are finally modeled by a ring whose inner diameter varies over time. Opening and closure timing are synchronized with patient data. FIG. 7 illustrates a synthetic model of valve dynamics for CFD boundary conditions. As shown in FIG. 7, each valve 702 and 704 is modeling by a ring or annulus whose inner diameter varies over time to represent opening and closing of the valve.

Figure 8:
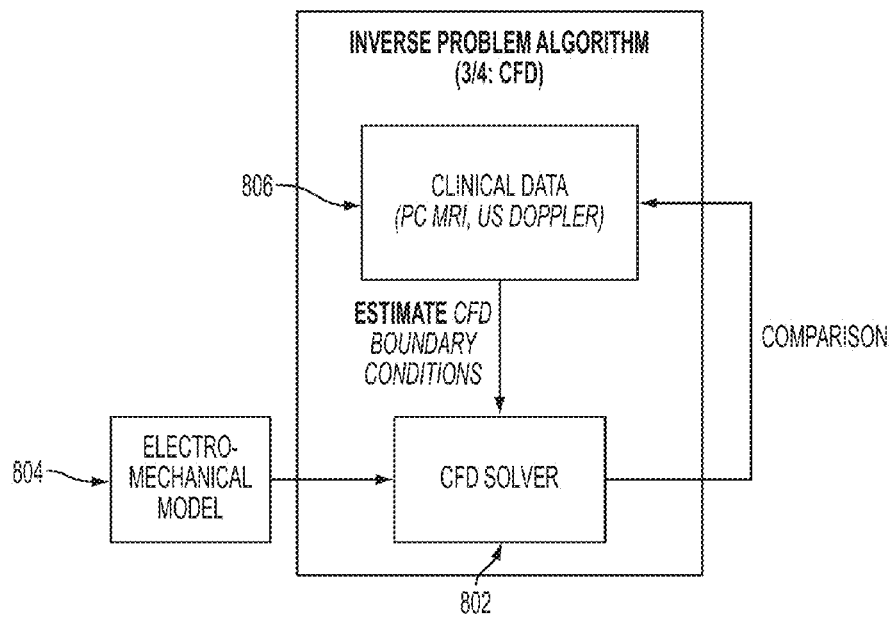
FIG. 8 illustrates a framework for determining the initial patient-specific CFD boundary conditions.

CFD boundary conditions are personalized from clinical data directly. Measured inflows and outflows are provided as input to the model. This data is useful in recovering patient-specific aortic/pulmonary pressures, which is done at every FSI simulation step by enforcing that the simulated flow due to endocardial pressurization matches the measured flow. FIG. 8 illustrates a framework for determining the initial patient-specific CFD boundary conditions. As illustrated in FIG. 8, the electromechanical model 804 (i.e., the electrophysiology model and the biomechanics model) with the initial patient-specific parameters (determined at steps 402 and 404) simulate the movement of the ventricles and is coupled with the CFD solver 802. The CFD solver 802 simulates blood flow into and out of the ventricles. The simulated blood flow is compared with clinical data 806 providing blood flow measurements (e.g., PC MRI or Ultrasound Doppler), and the CFD boundary conditions are adjusted using an inverse problem algorithm to best match the simulated blood flow with the observed clinical data 806, resulting in the initial patient-specific CFD boundary conditions.

Returning to FIG. 4, at step 408, a coupled FSI simulation is performed using the initial parameters for the electrophysiology model, the biomechanics model, and the CFD boundary conditions. The electrophysiology model, the biomechanics model, and the CFD solver are computed sequentially at each time step dt of the simulation. FIG. 9 illustrates a framework for implementing the coupled FSI simulation according to an embodiment of the present invention. As illustrated in FIG. 9, a multi-physics solver 900 having patient-specific parameters 901 performs the FSI simulation. At each time step dt, the EP solver 902, the CSM solver 906, and the CFD solver 910 are sequentially invoked. In particular, at a given time t, the following operations are performed. First, the trans-membrane voltage v(t+dt) at the next time t+dt is calculated by the EP solver 902. An Euler semi-implicit scheme can be used for numerical stability. The strength of the active force $F_c$(t+dt) is then computed by the electro-mechanical coupling interface 904. The active force $F_c$(t+dt) is applied to the dynamics system of Equation (2) by the CSM solver 906 to calculate positions U(t+dt) of the mesh, under the current pressure $F_p$(t). Here also, an Euler semi-implicit scheme can be used for numerical stability. The displacements U(t+dt)−U(t) and velocities (U(t+dt)−U(t))/dt are given to the CFD solver 910 by the fluid-structure coupling interface 908, and the CFD solver 910 calculates the new state of the blood flow, and therefore new pressure values $F_p$(t+dt), which are provided to the CSM solver 906 by the fluid-structure coupling interface 908. These operations are performed for a plurality of time steps over a time period, resulting in a simulation of ventricle movement and blood flow of that period. In an alternative implementation, the CSM solver 906 and the CFD solver 910 can be iteratively invoked within a time step until convergence, in order to provide a stronger fluid-structure coupling.

Returning to FIG. 4, at step 410, the initial parameters for the electrophysiology model, the biomechanics model, and the CFD parameters are refined based on the coupled FSI simulation. Marginalizing the models to adjust their parameters may not yield the optimal estimates. The final stage in generating the patient-specific computation heart model refines the estimated parameters by considering the fully-coupled system at once using multivariate inverse problem algorithms. FIG. 10 illustrates a framework for refining the patient-specific parameters of the computation heart model according to an embodiment of the present invention. As illustrated in FIG. 10, the multi-physics solver 1002, which is analogous to the multi-physics solver 900 illustrated in detail in FIG. 9, simulated ventricular movement and blood flow. The simulation results are compared to the clinical data 1004, including medical image data and other non-imaging clinical data, as described above, and the patient-specific parameters for the electrophysiology model, the biomechanics model, and the CFD boundary conditions are refined using a multivariate inverse problem algorithm to best match the simulation results to the clinical data 1004. For example, a multivariate inverse problem algorithm such as the algorithm described in Powell, "Developments of NEWUOA for Minimization Without Derivatives", *J. Num. Analysis,* 2008, which is incorporated herein by reference, but the present invention is not limited thereto. The result of the cardiac model is a set of patient-specific values for the model parameters, which constitute novel advanced cardiac measurements, and a moving mesh with blood flow simulation. From these meshes, one can compute ejection fraction, blood flow velocity, vorticity, stroke volume, electrophysiology parameters (ECG), regurgitations, etc., which can be used for therapy planning.

Figure 11:
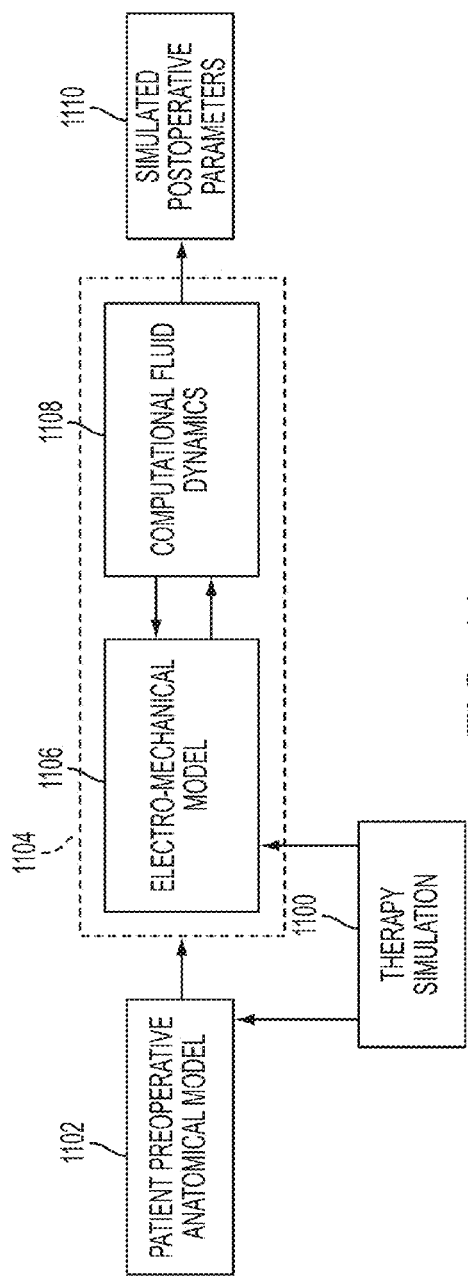
FIG. 11 illustrates a framework for implementing cardiac therapy simulation according to an embodiment of the present invention.

Returning to FIG. 1, at step 120, once the patient-specific computational heart model is generated, a cardiac therapy is simulated using the patient-specific computational heart model. FIG. 11 illustrates a framework for implementing cardiac therapy simulation according to an embodiment of the present invention. Once patient's heart model is estimated, it is perturbed to simulate therapies 1100 and compute postoperative surrogate predictors 1110 for planning. As shown in FIG. 11, the therapy simulation 1100 can perturb the patient-specific anatomical model 1102 or perturb the patient-specific computational model 1104. In an advantageous embodiment, surgeries can be simulated by enabling a user to interactively manipulate the anatomical model 1102. For example, resections are simulated by removing tetrahedra. Tissue can be dragged by the user, deformations being computed using the dynamics system defined in Equation 1. Fiber orientations are preserved by expressing them in terms of local barycentric coordinates per tetrahedra. Therapies acting on the cardiac function directly, like cardiac resynchronization therapy, can be simulated by perturbing the parameters of the electro-mechanical model 1106. Once the model is perturbed, a simulation of the perturbed system is performed using the patient-specific computational heart model 1104 (including the electro-mechanical model 1106 and the CFD 1108), without modifying the estimated patient-specific model parameters. The simulation can be performed using the framework of FIG. 9, as described above. The result of the simulation is a moving mesh with blood flow simulation.

Returning to FIG. 1, at step 130, the estimated parameters of the coupled multi-physics heart model, resulting from step 410 of FIG. 4, are presented to the user as advanced cardiac measurements, along with simulation results. As described above in the description of the method of FIG. 4, the advanced measurements can include, but are not limited to, tissue stiffness, active stress, electrical diffusivity, and parameters controlling action potential duration. Simulation results include a moving mesh that shows movement of the ventricles and a blood flow simulation. From these results, various parameters, such as ejection fraction, blood flow velocity and vorticity, stroke volume, electrophysiology (EP) parameters, regurgitations, etc., can be calculated for the simulated postoperative outcome. These parameters show the effect of the simulated cardiac therapy on the patient's heart function and blood flow. Various cardiac therapies can be simulated for a patient in order to provide simulated outcomes for each therapy, which would allow a physician to select the optimal therapy for that patient. Variations of a particular therapy can also be simulated for a patient to allow a physician to optimize a plan for a particular therapy for that patient.

Figure 12:
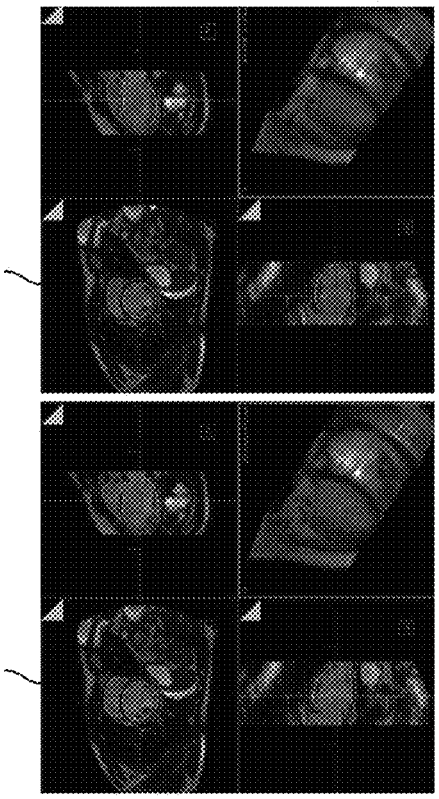
FIGS. 12-18 illustrate exemplary results of patient-specific heart simulation.
Figure 13:
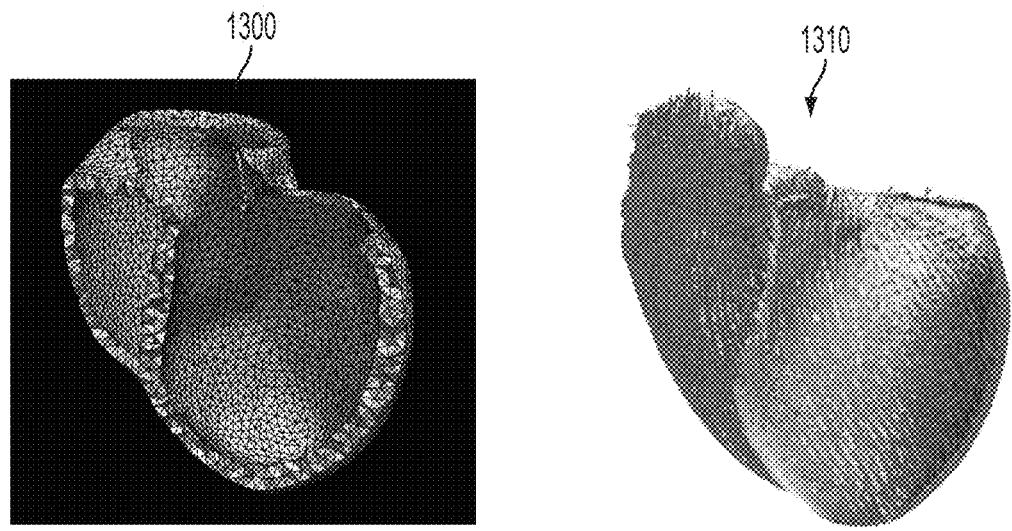
Figure 14:
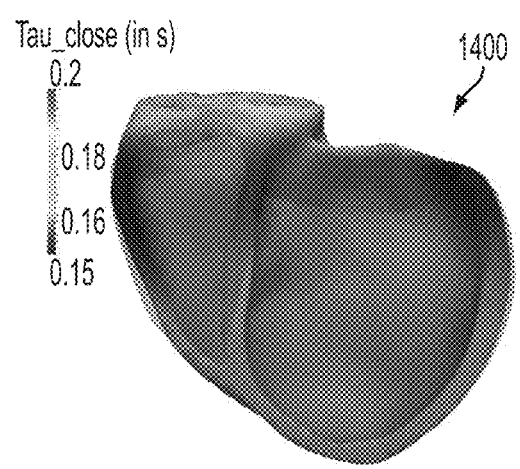

FIGS. 12-18 illustrate exemplary results for an FSI simulation for a patient with dilated cardiomyopathy. In this example, cardiac MR images were used to detect the LV and RV anatomies. FIG. 12 illustrates exemplary LV and RV detection results in cardiac MR images. As illustrated in FIG. 12, frames 1200 show the LV and RV detection results in end-diastolic frames, and frames 1210 show the LV and RV detection results in end-systolic frame. The patient-specific anatomical model was generated by fusing the two ventricles and generating synthetic fiber orientations, as in-vivo DTI was not available. FIG. 13 illustrates exemplary results for generating the anatomical model. As shown in FIG. 13, image 1300 shows the bi-ventricular myocardium mesh and image 13010 shows the computational model of fiber orientation. A spatially varying action potential duration (modeled by the free-parameter $\tau_{close}$) is mapped to the anatomical model to mimic the electrophysiology patterns observed in humans. FIG. 14 illustrates the map of $\tau_{close}$ values 1400 on the patient-specific anatomical model.

Figure 15:
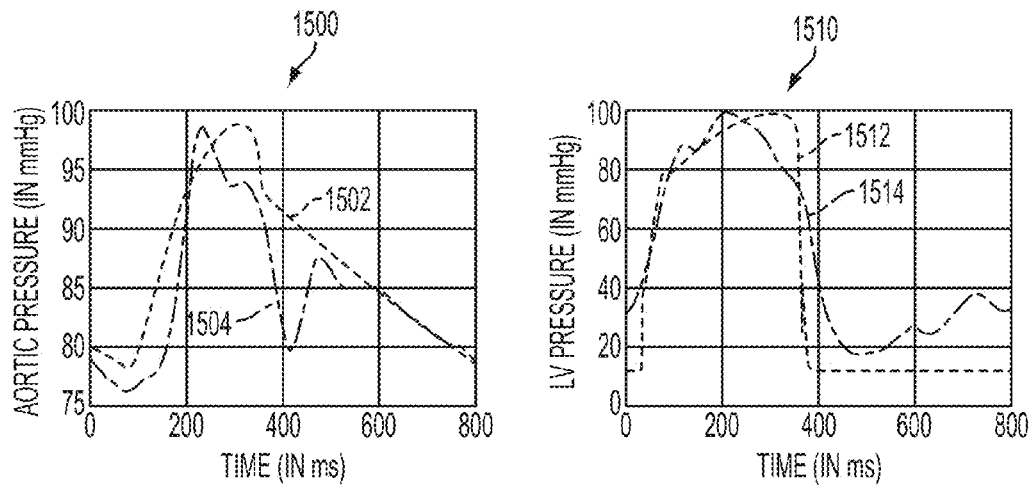
Figure 16:
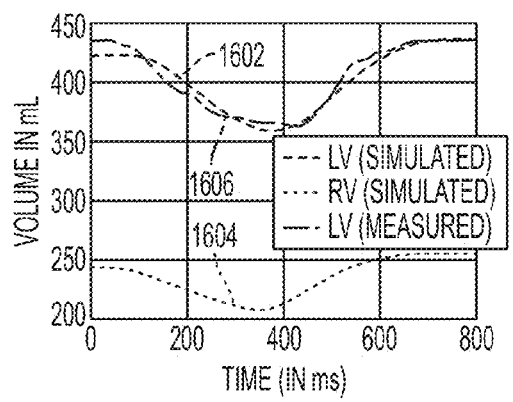

Pressure catheterization was available for this patient. Hence, the free parameters of the 3-element Windkessel model of the aorta were adjusted using an exhaustive search approach. Atrial pressures were set constant in this first experiment. Fluid-related parameters, such as flow and pressure are lumped at this stage. As no regurgitations were visible, arterial flow was equal to the opposite of the volume variation of the ventricle. FIG. 15 illustrates the simulated pressures overlaid with the measured values. As shown in FIG. 15, image 1500 illustrates simulated pressures 1502 and measured pressures 1504 of the aorta. Image 1510 illustrates simulated pressures 1512 and measured pressures 1514 of the left ventricle. As one can see, the 3-element Windkessel model could be personalized from the data to capture the main features of the pressure curve. The simulated pressure inside the ventricle was also fairly similar to the measured one, although no active atrial contraction was modeled in this preliminary experiment. It is also possible to adjust the strength of the active contraction $\sigma_0$, resulting in a qualitatively promising matching between simulated endocardial volume variation and measured one. FIG. 16 illustrates simulated volume curves for the LV 1602 and RV 1604 and a measured volume curve for the LV 1606. As shown in FIG. 16, adjusting the strength of the active contraction $\sigma_0$ results in capturing the observed volume variations of the LV.

Figure 17:
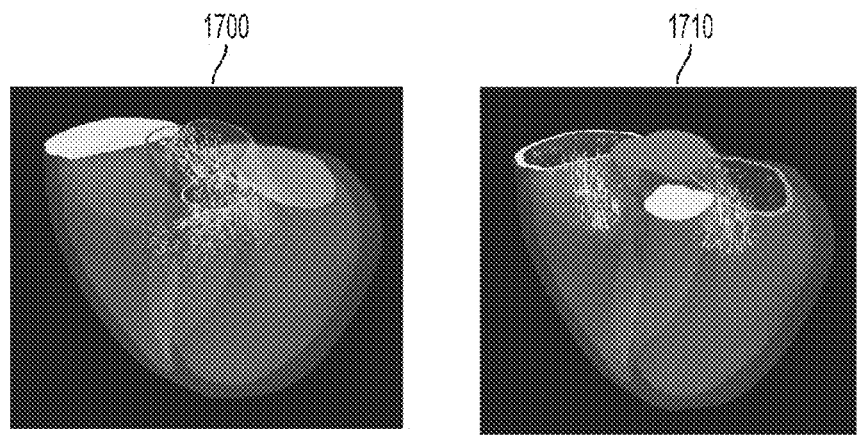
Figure 18:
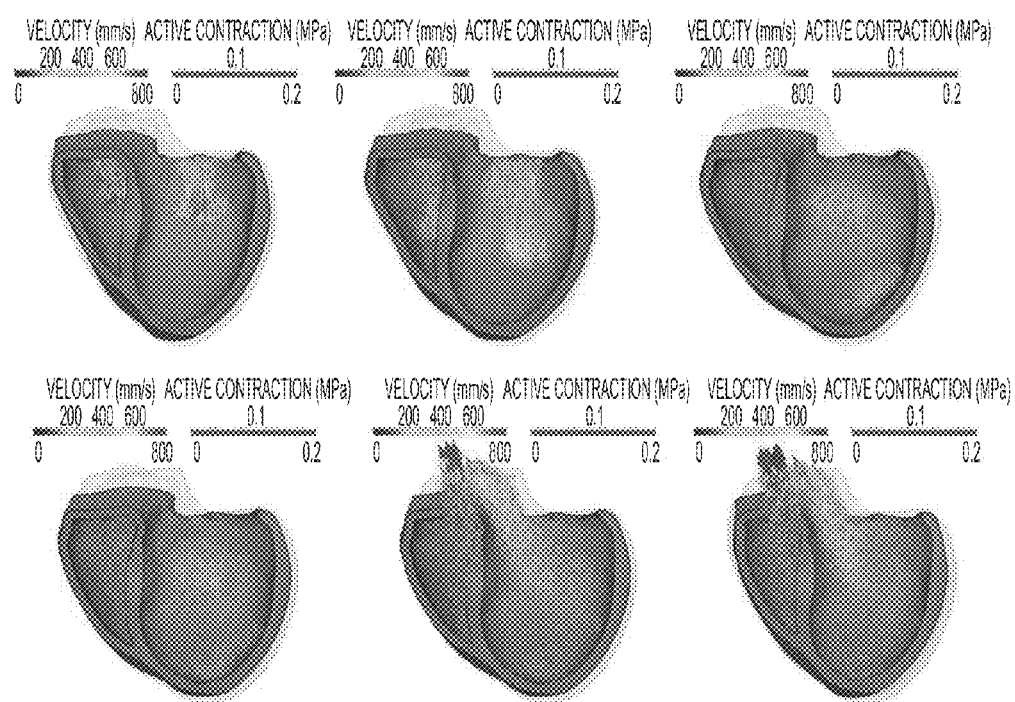

FIGS. 17 and 18 exemplary results of the FSI simulation. FIG. 14 shows simulated blood flow velocities computed at end-systole (1700) and end-diastole (1710). FIG. 18 shows simulated blood flow results.

Although above described methods are described as being implemented with two-way coupling between the electro-mechanical model and the CFD simulation, the present invention is not limited thereto, and it is possible to implement one-way coupling as well. In the case of one-way coupling between the electro-mechanical model and the CFD simulation, myocardium function can first be simulated entirely using only electro-mechanics models, with blood flow being modeled with lumped parameters. The resulting myocardium displacements and velocities are then given to the CFD solver.

Figure 19:
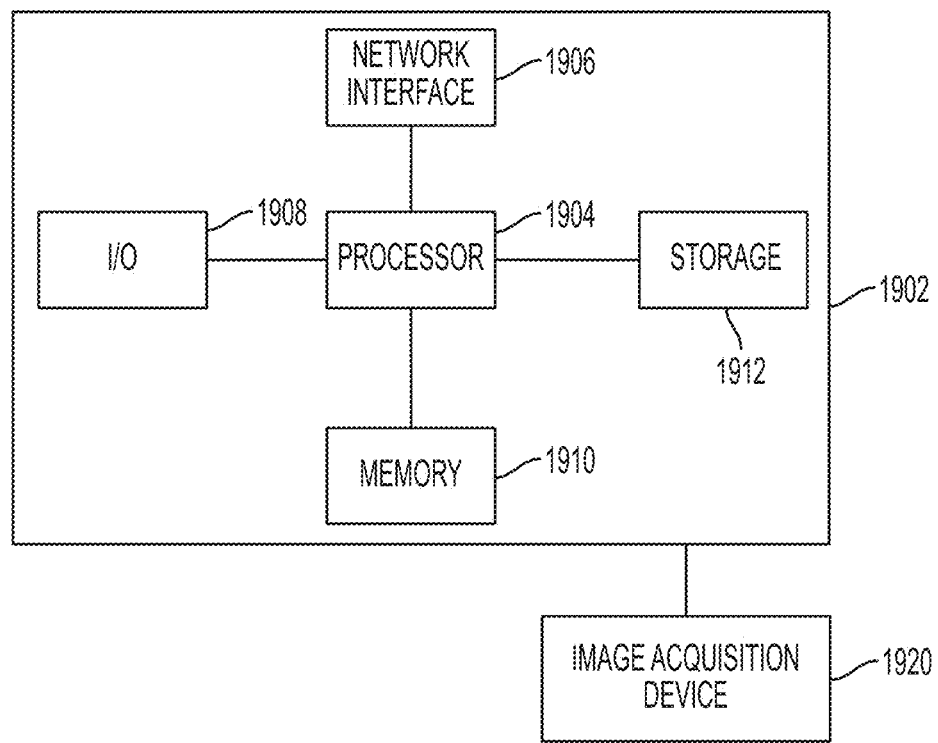
FIG. 19 is a high-level block diagram of a computer capable of implementing the present invention.

The above-described methods for generating a patient-specific anatomic model of the heart, generating a patient-specific computational model of the heart, and performing patient-specific cardiac therapy simulations can be implemented on a computer using well-known computer processors, memory units, storage devices, computer software, and other components. A high-level block diagram of such a computer is illustrated in FIG. 19. Computer 1902 contains a processor 1904, which controls the overall operation of the computer 1902 by executing computer program instructions which define such operation. The computer program instructions may be stored in a storage device 1912 (e.g., magnetic disk) and loaded into memory 1910 when execution of the computer program instructions is desired. Thus, the steps of the methods of FIGS. 1, 2, 3, 4, 5, 6, 8, 9, 10, and 11 may be defined by the computer program instructions stored in the memory 1910 and/or storage 1912 and controlled by the processor 1904 executing the computer program instructions. An image acquisition device 1920, such as an MR scanning device, Ultrasound device, etc., can be connected to the computer 1902 to input image data to the computer 1902. It is possible to implement the image acquisition device 1920 and the computer 1902 as one device. It is also possible that the image acquisition device 1920 and the computer 1902 communicate wirelessly through a network. The computer 1902 also includes one or more network interfaces 1906 for communicating with other devices via a network. The computer 1902 also includes other input/output devices 1908 that enable user interaction with the computer 1902 (e.g., display, keyboard, mouse, speakers, buttons, etc.). Such input/output devices 1908 may be used in conjunction with a set of computer programs as an annotation tool to annotate volumes received from the image acquisition device 1920. One skilled in the art will recognize that an implementation of an actual computer could contain other components as well, and that FIG. 19 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for computing advanced cardiac measurements from clinical data and medical images and performing therapy planning based on a patient-specific multi-physics heart model, the method comprising:
   generating a patient-specific anatomical model of left and right ventricles from medical image data of a patient;
   generating a patient-specific computational heart model, which couples a biomechanics model, an electrophysiology model and a hemodynamic model together, based on the patient-specific anatomical model of the left and right ventricles and patient-specific clinical data by:
      determining initial patient-specific parameters of an electrophysiology model,
      determining initial patient-specific parameters of a biomechanics model,
      determining initial patient-specific computational fluid dynamics (CFD) boundary conditions,
      performing a coupled fluid-structure interaction (FSI) simulation using the initial patient-specific parameters of the electrophysiology model, the initial patient-specific parameters of the biomechanics model, and the initial patient-specific CFD boundary conditions, and
      refining the initial patient-specific parameters of the electrophysiology model, the initial patient-specific parameters of the biomechanics model, and the initial patient-specific CFD boundary conditions based on the coupled FSI simulation, wherein the refined parameters define a set of advanced cardiac measurements; and
   simulating at least one cardiac therapy using the patient-specific computational heart model.

2. The method of claim 1, wherein the step of generating a patient-specific anatomical model of left and right ventricles from medical image data of a patient comprises:
   detecting a patient-specific left ventricle model and a patient-specific right ventricle model in the medical image data; and
   fusing the left ventricle model and the right ventricle model into a single bi-ventricular volumetric mesh.

3. The method of claim 2, wherein the step of generating a patient-specific anatomical model of left and right ventricles from medical image data of a patient further comprises:

mapping spatial information corresponding to at least one of scars, grey zones, or fibrosis identified from magnetic resonance (MR) sequences onto a tetrahedral representation of bi-ventricular volumetric mesh.

4. The method of claim 3, wherein the MR sequence is one of a delayed enhanced MR sequence or a time interval (T1) weighted MR sequence.

5. The method of claim 2, wherein the step of generating a patient-specific anatomical model of left and right ventricles from medical image data of a patient further comprises:
registering a tensor field of an in-vivo diffusion tensor magnetic resonance image of cardiac fibers to the bi-ventricular volumetric mesh.

6. The method of claim 2, wherein the step of generating a patient-specific anatomical model of left and right ventricles from medical image data of a patient further comprises:
generating a model of fiber architecture based on the bi-ventricular volumetric mesh.

7. The method of claim 1, wherein the step of determining initial patient-specific parameters of an electrophysiology model comprises:
determining the initial patient-specific parameters of the electrophysiology model based on an inverse problem method that relies on an uncoupled electrophysiology solver and patient-specific electrophysiology data.

8. The method of claim 7, wherein the step of determining the initial patient-specific parameters of the electrophysiology model based on an inverse problem method that relies on an uncoupled electrophysiology solver and patient-specific electrophysiology data comprises:
adjusting a tissue diffusivity parameter of the electrophysiology model based on measured echo cardiogram (ECG) data of the patient; and
adjusting a parameter controlling local tissue diffusivity and an action potential duration of the electrophysiology model based on patient-specific endocardial mappings.

9. The method of claim 1, wherein the step of determining initial patient-specific parameters of a biomechanics model comprises:
simulating motion of the patient-specific anatomical model using a computational solid mechanics (CSM) solver coupled with the electrophysiology model with the determined initial patient-specific parameters and a lumped hemodynamics model; and
determining the initial patient-specific parameters of the biomechanics model based on an inverse problem method that compares simulated cardiac motion and cardiac motion measurements performed on dynamic medical images.

10. The method of claim 9, wherein the step of determining the initial patient-specific parameters of the biomechanics model based on an inverse problem method that compares simulated cardiac motion and cardiac motion measurements performed on dynamic medical images comprises:
estimating at least one of tissue stiffness, active stress, relaxation or contraction rates.

11. The method of claim 1, wherein the step of determining initial patient-specific computational fluid dynamics (CFD) boundary conditions comprises:
simulating blood flow using a CFD solver coupled to an electro-mechanical model with the determined initial patient-specific parameters of the electrophysiology model and the initial determined patient-specific parameters of the biomechanics model; and
determining the initial CFD boundary conditions based on an inverse problem method that compares the simulated blood flow with blood flow measurements in the clinical data and medical images.

12. The method of claim 1, wherein the step of performing a coupled fluid-structure interaction (FSI) simulation using the initial patient-specific parameters of the electrophysiology model, the initial patient-specific parameters of the biomechanics model, and the initial patient-specific CFD boundary conditions comprises, at each time t:
calculating a trans-membrane voltage v(t+dt) at a next time t+dt using the initial patient-specific parameters of the electrophysiology model;
calculating an active force $F_c$(t+dt) for the next time based on the trans-membrane voltage v(t+dt) using the initial patient-specific parameters of the biomechanics model;
calculating positions U(t+dt) of mesh points of the patient-specific anatomical model for the next time based on the active force $F_c$(t+dt) and under a current pressure $F_p$(t) using the initial patient-specific parameters of the biomechanics model; and
calculating blood flow for the next time through a CFD solver based on displacements U(t+dt)−U(t) and velocities (U(t+dt)−U(t))/dt of the mesh points of the patient-specific anatomical model using the initial patient-specific CFD boundary conditions, wherein the blood flow simulation calculates a pressure $F_p$(t+dt) for the next time.

13. The method of claim 1, wherein the step of refining the initial patient-specific parameters of the electrophysiology model, the initial patient-specific parameters of the biomechanics model, and the initial patient-specific CFD boundary conditions based on the coupled FSI simulation comprises:
refining the initial patient-specific parameters of the electrophysiology model, the initial patient-specific parameters of the biomechanics model, and the initial patient-specific CFD boundary conditions based on a multivariate inverse problem method that compares the simulation results of the coupled FSI simulation in terms of cardiac motion and blood flow with the cardiac motion and blood flow measured from the clinical data, to minimize the discrepancy between the simulations results and the clinical data.

14. The method of claim 1, wherein the step of simulating at least one cardiac therapy using the patient-specific computational heart model comprises:
perturbing at least one of the patient-specific anatomical model or the patient-specific computational heart model to represent the at least one cardiac therapy; and
performing an FSI simulation of heart function and blood flow based on the perturbed at least one of the patient-specific anatomical model or the patient-specific computational heart model using the refined patient-specific parameters for the electrophysiology model, biomechanics model, and CFD boundary conditions.

15. The method of claim 14, further comprising:
calculating at least one clinical cardiac parameter based on the simulated heart function and blood flow to represent effect of the simulated at least one cardiac therapy.

16. The method of claim 15, wherein the step of calculating at least one clinical cardiac parameter based on the simulated heart function and blood flow to represent effect of the simulated at least one cardiac therapy comprises:
calculating at least one of ejection fraction, blood flow velocity, blood flow vorticity, stroke volume, electrophysiology parameters, regurgitations based on the simulated heart function and blood flow.

17. The method of claim 1, further comprising:
outputting the set of advanced cardiac measurements.

18. An apparatus for computing advanced cardiac measurements from clinical data and medical images and performing therapy planning based on a patient-specific multi-physics heart model, the method comprising:
means for generating a patient-specific anatomical model of left and right ventricles from medical image data of a patient;
means for generating a patient-specific computational heart model, which couples a biomechanics model, an electrophysiology model and a hemodynamic model together, based on the patient-specific anatomical model of the left and right ventricles and patient-specific clinical data, comprising:
means for determining initial patient-specific parameters of an electrophysiology model,
means for determining initial patient-specific parameters of a biomechanics model,
means for determining initial patient-specific computational fluid dynamics (CFD) boundary conditions,
means for performing a coupled fluid-structure interaction (FSI) simulation using the initial patient-specific parameters of the electrophysiology model, the initial patient-specific parameters of the biomechanics model, and the initial patient-specific CFD boundary conditions, and
means for refining the initial patient-specific parameters of the electrophysiology model, the initial patient-specific parameters of the biomechanics model, and the initial patient-specific CFD boundary conditions based on the coupled FSI simulation, wherein the refined parameters define a set of advanced cardiac measurements; and
means for simulating at least one cardiac therapy using the patient-specific computational heart model.

19. The apparatus of claim 18, wherein the means for determining initial patient-specific parameters of an electrophysiology model comprises:
means for determining the initial patient-specific parameters of the electrophysiology model based on a comparison of cardiac electrophysiology simulation results using uncoupled electrophysiology solver with the patient-specific clinical data.

20. The apparatus of claim 18, wherein the means for determining initial patient-specific parameters of a biomechanics model comprises:
means for simulating motion of the patient-specific anatomical model using a computational solid mechanics (CSM) solver coupled with the electrophysiology model with the determined initial patient-specific parameters and a lumped hemodynamics model; and
means for determining the initial patient-specific parameters of the biomechanics model based on a comparison of the simulated motion of the patient-specific anatomical model with patient-specific dynamic medical images.

21. The apparatus of claim 18, wherein the means for determining initial patient-specific computational fluid dynamics (CFD) boundary conditions comprises:
means for simulating blood flow using a CFD solver coupled to an electro-mechanical model with the determined initial patient-specific parameters of the electrophysiology model and the initial determined patient-specific parameters of the biomechanics model; and
means for determining the initial CFD boundary conditions based on a comparison of the simulated blood flow with the clinical data.

22. The apparatus of claim 18, wherein the means for refining the initial patient-specific parameters of the electrophysiology model, the initial patient-specific parameters of the biomechanics model, and the initial patient-specific CFD boundary conditions based on the coupled FSI simulation comprises:
means for refining the initial patient-specific parameters of the electrophysiology model, the initial patient-specific parameters of the biomechanics model, and the initial patient-specific CFD boundary conditions based on a comparison of FSI simulation results in terms of cardiac motion and blood flow with the clinical data to minimize a difference between simulated cardiac motion and blood flow and observed cardiac motion and blood flow in the clinical data.

23. The apparatus of claim 18, wherein the means for simulating at least one cardiac therapy using the patient-specific computational heart model comprises:
means for perturbing at least one of the patient-specific anatomical model or the patient-specific computational heart model to represent the at least one cardiac therapy; and
means for performing an FSI simulation of heart function and blood flow based on the perturbed at least one of the patient-specific anatomical model or the patient-specific computational heart model using the refined patient-specific parameters for the electrophysiology model, biomechanics model, and CFD boundary conditions.

24. A non-transitory computer readable medium storing computer program instructions for computing advanced cardiac parameters and planning therapies using a patient-specific multi-physics heart model, the computer program instructions, when executed on a processor, cause the processor to perform operations comprising:
generating a patient-specific anatomical model of left and right ventricles from medical image data of a patient;
generating a patient-specific computational heart model, which comprises an electrophysiology model, a biomechanics model and a hemodynamic model, based on the patient-specific anatomical model of the left and right ventricles and patient-specific clinical data by:
determining initial patient-specific parameters of an electrophysiology model,
determining initial patient-specific parameters of a biomechanics model,
determining initial patient-specific computational fluid dynamics (CFD) boundary conditions,
performing a coupled fluid-structure interaction (FSI) simulation using the initial patient-specific parameters of the electrophysiology model, the initial patient-specific parameters of the biomechanics model, and the initial patient-specific CFD boundary conditions, and
refining the initial patient-specific parameters of the electrophysiology model, the initial patient-specific parameters of the biomechanics model, and the initial patient-specific CFD boundary conditions based on the coupled FSI simulation, wherein the refined parameters define a set of advanced cardiac measurements; and
simulating at least one cardiac therapy using the patient-specific computational heart model.

25. The non-transitory computer readable medium of claim 24, wherein the operation of determining initial patient-specific parameters of an electrophysiology model comprises:
   determining the initial patient-specific parameters of the electrophysiology model based on an inverse problem method that compares cardiac electrophysiology simulation results obtained using an uncoupled electrophysiology solver with the patient-specific clinical data.

26. The non-transitory computer readable medium of claim 24, wherein the operation of determining the initial patient-specific parameters of the electrophysiology model based on an inverse problem method that compares cardiac electrophysiology simulation results obtained using an uncoupled electrophysiology solver with the patient-specific clinical data comprises:
   adjusting a tissue diffusivity parameter of the electrophysiology model based on measured echo cardiogram (ECG) data of the patient; and
   adjusting a parameter controlling local tissue diffusivity and action potential duration of the electrophysiology model based on patient-specific endocardial mappings.

27. The non-transitory computer readable medium of claim 24, wherein the operation of determining initial patient-specific parameters of a biomechanics model comprises:
   simulating motion of the patient-specific anatomical model using a computational solid mechanics (CSM) solver coupled with the electrophysiology model with the determined initial patient-specific parameters and a lumped hemodynamics model; and
   determining the initial patient-specific parameters of the biomechanics model based on an inverse problem method that compares the simulated motion of the patient-specific anatomical model with the cardiac motion measured from patient-specific dynamic medical images.

28. The non-transitory computer readable medium of claim 27, wherein the operation of determining the initial patient-specific parameters of the biomechanics model based on an inverse problem method that compares the simulated motion of the patient-specific anatomical model with the cardiac motion measured from patient-specific dynamic medical images comprises:
   estimating at least one of tissue stiffness, active stress, relaxation, or contraction rates.

29. The non-transitory computer readable medium of claim 24, wherein the operation of determining initial patient-specific computational fluid dynamics (CFD) boundary conditions comprises:
   simulating blood flow using a CFD solver coupled to an electro-mechanical model with the determined initial patient-specific parameters of the electrophysiology model and the initial determined patient-specific parameters of the biomechanics model; and
   determining the initial CFD boundary conditions based on an inverse problem method that compares the simulated blood flow with blood flow measurements in the clinical data and medical images.

30. The non-transitory computer readable medium of claim 24, wherein the operation of performing a coupled fluid-structure interaction (FSI) simulation using the initial patient-specific parameters of the electrophysiology model, the initial patient-specific parameters of the biomechanics model, and the initial patient-specific CFD boundary conditions comprises, at each time t:
   calculating a trans-membrane voltage v(t+dt) at a next time t+dt using the initial patient-specific parameters of the electrophysiology model;
   calculating an active force $F_c$(t+dt) for the next time based on the trans-membrane voltage v(t+dt) using the initial patient-specific parameters of the biomechanics model;
   calculating positions U(t+dt) mesh points of the patient-specific anatomical model for the next time based on the active force $F_c$(t+dt) and under a current pressure $F_p$(t) using the initial patient-specific parameters of the biomechanics model; and
   calculating blood flow for the next time through a CFD solver based on displacements U(t+dt)−U(t) and velocities (U(t+dt)−U(t))/dt of the mesh points of the patient-specific anatomical model using the initial patient-specific CFD boundary conditions, wherein the blood flow simulation calculates a pressure $F_p$(t+dt) for the next time.

31. The non-transitory computer readable medium of claim 24, wherein the operation of refining the initial patient-specific parameters of the electrophysiology model, the initial patient-specific parameters of the biomechanics model, and the initial patient-specific CFD boundary conditions based on the coupled FSI simulation comprises:
   refining the initial patient-specific parameters of the electrophysiology model, the initial patient-specific parameters of the biomechanics model, and the initial patient-specific CFD boundary conditions based on a multivariate inverse problems that compares simulation results of the coupled FSI simulation with the clinical data in terms of cardiac motion and blood flow.

32. The non-transitory computer readable medium of claim 24, wherein the operation of simulating at least one cardiac therapy using the patient-specific computational heart model comprises:
   perturbing at least one of the patient-specific anatomical model or the patient-specific computational heart model to represent the at least one cardiac therapy; and
   performing an FSI simulation of heart function and blood flow based on the perturbed at least one of the patient-specific anatomical model or the patient-specific computational heart model using the refined patient-specific parameters for the electrophysiology model, biomechanics model, and CFD boundary conditions.

33. The non-transitory computer readable medium of claim 32, wherein the operations further comprise:
   calculating at least one clinical cardiac parameter based on the simulated heart function and blood flow to represent effect of the simulated at least one cardiac therapy.

* * * * *